United States Patent [19]

Harder et al.

[11] Patent Number: 4,790,854
[45] Date of Patent: * Dec. 13, 1988

[54] BONE PROSTHESIS ASSEMBLY

[75] Inventors: Hans E. Harder, Probsteierhagen; Klaus Behrens, Rickling, both of Fed. Rep. of Germany; Rainer Kotz, Vienna, Austria

[73] Assignee: Howmedica International Inc., Kiel, Fed. Rep. of Germany

[*] Notice: The portion of the term of this patent subsequent to Mar. 25, 2003 has been disclaimed.

[21] Appl. No.: 170,192

[22] Filed: Mar. 18, 1988

Related U.S. Application Data

[60] Continuation of Ser. No. 841,410, Mar. 19, 1986, Pat. No. 4,764,171, which is a division of Ser. No. 381,607, May 24, 1982, Pat. No. 4,578,081.

[51] Int. Cl.[4] ............ A61F 2/38; A61F 2/36
[52] U.S. Cl. ............................ 623/20; 623/23
[58] Field of Search ..................... 623/16, 18–23

[56] References Cited

U.S. PATENT DOCUMENTS

4,404,691  9/1983  Buning et al. .................. 623/20
4,578,081  3/1986  Harder et al. .................. 623/20

Primary Examiner—Ronald L. Frinks
Attorney, Agent, or Firm—Peter C. Richardson; Lawrence C. Akers; Mark Dryer

[57] ABSTRACT

A bone prosthesis comprising at least one joint component replacing a natural joint half, which is provided with a shank adapted to be connected to the bone, wherein a set of joint components is provided, and the shank is designed as a bone replacement member, with a connection portion provided adapted to be connected to the bone at one end and at the other end to the shank.

5 Claims, 7 Drawing Sheets

BONE PROSTHESIS ASSEMBLY

This is a continuation of application Ser. No. 841,410, filed on Mar. 19, 1986, now U.S. Pat. No. 4,764,171, which is a division of application Ser. No. 381,607 filed on May 24, 1982, now U.S. Pat. No. 4,578,081.

The present invention is an improvement over the invention disclosed and claimed in copending, commonly assigned application Ser. No. 238,013, filed Feb. 25, 1981, entitled "Modular Prosthesis Assembly", now U.S. Pat. No. 4,404,691.

Various endoprosthetic joints have become known for replacement of damaged or destroyed joint members, which are implanted in the human body. So, there exist prosthetic hip joints, knee joints and upper arm prostheses and the like. The usual endoprosthetic joints are normally provided with a shank which is driven into a bone canal and is fastened therein, i.e. either with or without bone cement.

Conventional endoprosthetic joints can no longer be implanted if, due to a tumor, for example, not only the joint but also bone regions adjacent the joint have been affected. In this case, a surgeon is compelled to resect the affected bone portions. The usual endoprosthetic joint portions are then no longer able to find any support at the bone.

In connection with the resection of bone portions affected by tumor it has become known to replace the resected region by a replacement portion. The replacement portion is made by hand. Between the diagnosis and the completion of the specific bone replacement portion, oftentimes, three weeks and more elapse. In this connection the danger exists that due to the progressing sickness of the bone the originally pre-calculated length of the bone replacement portion no longer suffices because the tumor has progressed too far. Besides, it is understandable that the production costs for bone replacement portions made by hand are extremely high.

It is the object of the invention to provide a bone prosthesis for the extremities, which is adapted to be universally implanted as a modular system, especially in connection with resections of joint portions with adjacent bone regions.

The modular bone prosthesis according to the invention provides a set of joint components of staggered shaft lengths. The shafts of the joint components, in this arrangement, are formed as replacement bone members which are connected with the non-resected bone with the aid of a suitable connection portion. In this connection the invention starts from the fact that the bone tumor will as a rule appear adjacent a joint. Through the provision of a replacement of joint components having staggered lengths it is possible to perform an adaptation to the resected length and the length of the bone, respectively. If, in this arrangement, according to the invention, the connection portion, too, is provided in the form of a replacement member of staggered lengths, a large number of different lengths may be replaced with the aid of the bone prosthesis according to the invention. If, for the joint component and the connection portion three lengths are respectively provided, nine different possibilities may be obtained for the overall length of the two parts. With the aid of a variable connection portion it is possible, besides, to effect an adaptation to the bone growth of juveniles, with the joint component allowed to remain in place.

In the case of the bone prosthesis according to the invention, the joint component may, for instance, be the femural joint part of an endoprosthetic hip joint. The spherical part of the joint may cooperate either with the natural acetabulum or with an implanted artificial cap.

In order to effect an adaptation to different hip joint conditions in connection with an equally dimensioned joint component, the joint component may be provided with a conical neck portion to accommodate a spherical joint part with inner cone in frictional engagement. This, however, is known in connection with conventional endoprosthetic hip joints.

The femural joint component may furthermore be provided with a clamping surface in the trochanter region against which a small plate may be clamped with the aid of one or several screws for the effective fixation of sinews. The clamping surface is preferably roughened, for instance, made madreporic in order to improve the concrescence of the sinews with the clamping surface. Another possibility of connection to the sinews is provided by a rib disposed opposite to the clamping surface which is formed integrally with the femural joint part and is provided with at least one transverse bore.

The joint component may furthermore be the femural joint part of a knee joint endoprosthesis. In this case, the portion adjacent the joint is preferably formed to resemble the natural distal femur with its condyles and is at the same time provided with a trough for the accommodation of the natural patella. The femural joint part may be connected to a tibial joint part of the knee joint endoprosthesis via a shank connected joint connection. The tibial part of the joint may be designed in any suitable manner and may be provided with a shank, for instance, which is driven into the tibia. For the purpose of an attachment in connection with the axis the tibial part of the joint is preferably provided with an annular-cylindrical joint attachment portion which engages within a joint recess of the femural part of the joint. A joint sleeve, preferably of synthetic material, is inserted into the joint attachment portion from opposite sides with radial flanges disposed outside which lie against the wall of the joint recess. A joint pin is pushed through the aligned openings of femural and tibial joint components and secured axially.

The tibial joint component may comprise a radial plate having inwardly projecting tongues integrally formed thereat laterally and medially. The tongues which are preferably provided with openings, serve to fasten the tibial joint component exteriorly at the tibia, with the shank seated in the bone canal in pressfit engagement. In this connection, bone cement may be omitted. If the shank is provided with a through passage aligned with the openings in the tongues, fixation may be effected transversely through the bone and the tibial joint component. The plate is furthermore preferably provided with several projections on the underside thereof, which are impressed into the tibia plateau in order to take care of a further fixation of the tibial joint component.

The joint component may, vice versa, be the tibial joint part of a knee joint endoprosthesis. In this case, the femural joint part can be connected by a bone replacement member having a joint recess or a femural joint part provided with a shank, i.e. by an articulated attachment connected to the axis, for example.

Also the region of the tibial joint part adjacent the plateau may be provided with a small clamping plate in the front for the purpose sinew fixation. To attach the fibula, an indentation may furthermore be formed in the tibial joint part with a web bridging the indentation.

As mentioned above, the femoral joint part may comprise a shank which is beaten into the distal femural canal. Preferably, the latter is provided with a tongue extending in parallel with the shank and having an aperture formed therein for the accommodation of a screw.

There are different possibilities to effect the connection between joint components and connection portions. What is especially advantageous is the use of a conical connection in which, for example, the joint component contains the inner cone and the connection portion contains the outer cone. The cone angle, in this arrangement, is selected to be such that a self-locking effect occurs. That means that a considerable torque may be transmitted between the interconnected parts an a retention force is also available to prevent the parts from moving apart from each other. The conical connection, in this arrangement, is selected to be the same in dimension for all the parts to be connected, independently of the length or the other dimensions of the prosthesis components.

For better adaptation to resected bone regions of different lengths a set of elongation pieces of staggered lengths may furthermore be provided. In addition, it is advantageous to provide a bipartite connection portion such that the parts of said connection portion are adapted to be detached and separated transversely of the longitudinal axis. If, for instance, the length of the prosthesis is no longer great enough owing to bone growth, a longer piece of elongation may be inserted. With a conical or plug-in type connection, in this arrangement, the sinews and muscles would have to be extraordinarily stretched, in order to make the individual plug-in type connections. A lateral separation and recomposition eliminates such a complicated precautionary measure.

The elongation piece preferably is provided with an inner cone at the one end and an outer cone at the other end, while the connection portion is provided with an outer cone at either end.

The elongated prosthesis parts are preferably tubular and of the same outer diameter. The material used must be well compatible with the tissue, and may be a suitable chromium-nickel alloy, for example.

In order to avoid rotation of the prosthesis parts facing each other, a key and keyway connection is preferably provided, for instance, in the form of paraxial nose-like formations at one end engaging within suitable recesses at the neighbouring end.

Examples of embodiment of the invention will be explained in the following in more detail by way of drawings.

Prior to enlarging on the individual representations in the drawings it is to be stated that each of the features described and shown is of inventively essential importance by itself and in connection with features of the claims.

FIGS. 1 to 12 show a first embodiment of a modular system for a bone endoprosthesis. Another embodiment of a modular system is shown in FIGS. 13 to 33. To begin with, the first system is to be enlarged upon.

Figure 1:
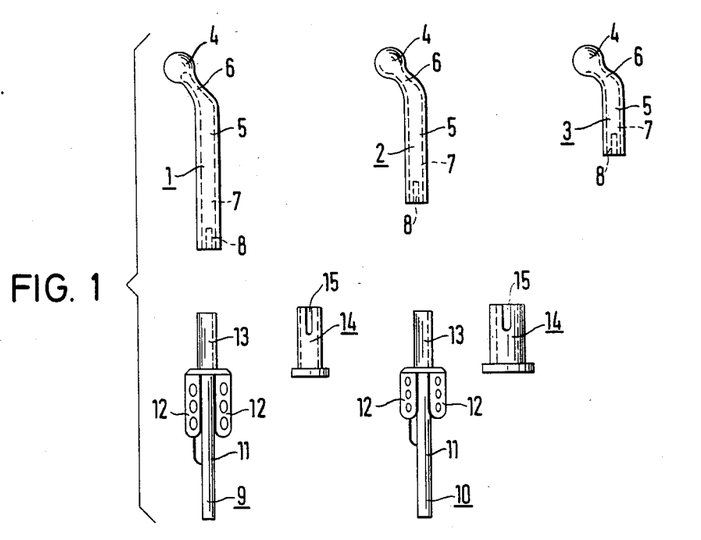
FIG. 1 is a diagrammatic representation of a set of components which can be used together to provide a hip prosthesis.

FIG. 1 shows the various components which can be made up to provide a hip prosthesis assembly according to the invention.

This prosthesis consists basically of a joint component, in this case a hip component, and a mounting component. In FIG. 1 three hip components are shown indicated by reference numerals 1, 2 and 3. Each hip component comprises a head 4 which is connected to a connection part 5 through a neck 6. In the arrangement being described each of the hip components has a 32 mm head and a standard neck length and can be used as a total hip or with a bicentric floating head. The connection portions are arranged in different lengths so that three hip component sizes are available, 110 mm, 150 mm and 190 mm.

The hip components are hollow so that the support portions which are cylindrical provide a socket 7 in which is located a key 8.

The hip components are arranged for connection to the mounting components which are indicated by reference numerals 9 and 10. These mounting components have stems, indicated by reference numeral 11 and these stem diameters are, in the arrangement being described 14 mm and 16 mm, the stem length is 150 mm. The stems are of the Walldius type with three flanges which are indicated by reference numeral 12 in FIG. 1. The precise construction of the mounting components is more clearly shown in FIG. 10 from which it will be seen that one of the flanges 12 is longer than the other two. The mounting has a connection portion 13 which is in the form of a spigot.

The mounting component and the hip component may be made of any suitable material, for example Vitallium (Registered Trademark of Howmedica International Inc.).

Figure 10:
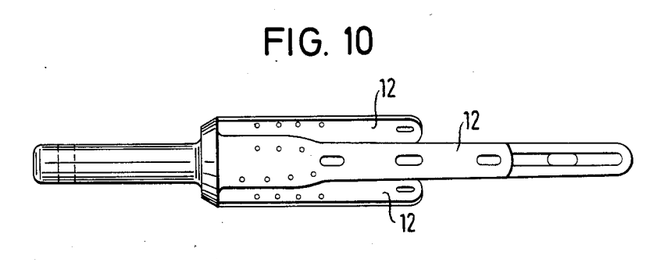
FIG. 10 is a side elevation of a mounting component.
Figure 11:
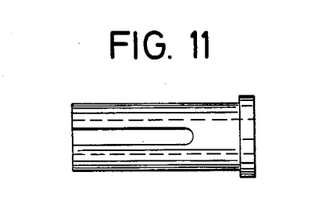
FIG. 11 is a side view of a sleeve for use with the component shown in FIG. 10.
Figure 12:
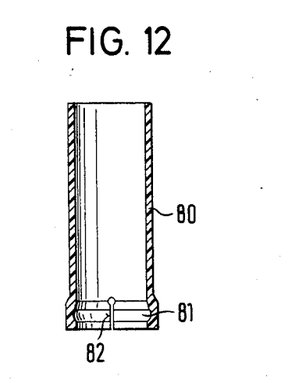
FIG. 12 is a cross-sectional side view of the retaining sleeve shown in FIG. 8.

Plastic sleeve 14 is a press fit over the spigot 13 so that it is effectively held against rotation. This sleeve 14 has a keyway 15 and the outer dimensions are such that the hip component can be pushed over the mounting component spigot 13 and the key 8 will engage the key way 15 in the sleeve thus preventing rotation between the components.

As three hip components are provided of different sizes and two mounting components a hip resection system is thus provided which allows for three resection lengths, that is 120 mm, 160 mm and 200 mm and with two optional stem diameters. The parts can be assembled in the operating theatre to the required length and to fit the femur as required.

Figure 2:
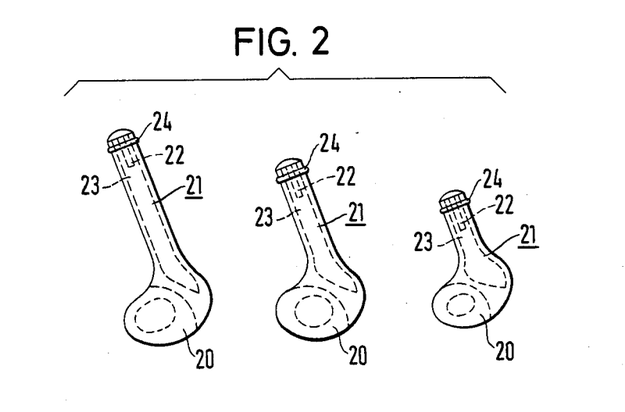
FIG. 2 is a diagrammatic representation of a set of femural knee components which can be used with the components shown in FIG. 1.

FIG. 2 shows a set of joint components, in this case femoral knee components which can be used on a spherocentric knee. A set of tibial components which can be used with the femoral knee components of FIG. 2 are shown in FIG. 3.

Figure 3:
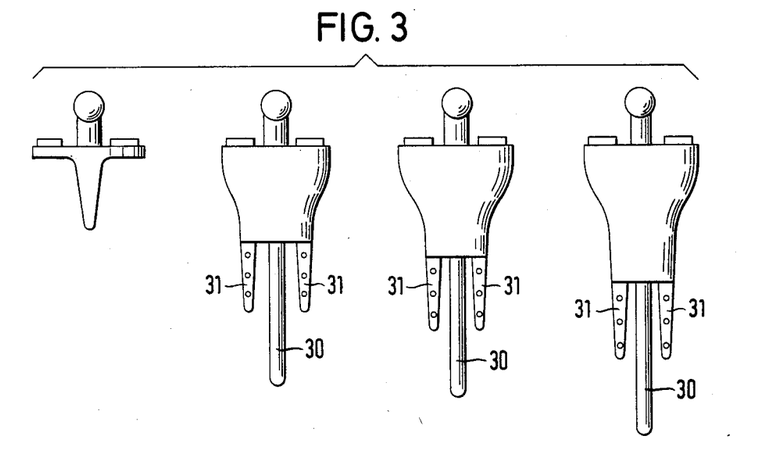
FIG. 3 is a diagrammatic representation of a set of tibial components which can be used with the femural components shown in FIG. 2.

A knee resection system according to the invention can therefore comprise two or more mounting components of the kind shown in FIG. 1, complete with mounting sleeves 14, one or more femoral knee components as shown in FIG. 2 and one or more tibial components as shown in FIG. 3.

Each of the femoral components comprises a head 20 of known shape and which not therefore be further described apart from stating that the portions which represent the condyles are made hollow and act as the engagement portion of the joint. This portion is connection to a connection part 21 which is again in the form of a hollow cylinder and of similar dimensions to the connection part 7 of the hip component shown in FIG. 1. A key 22 is again provided in each of the sockets 23 provided by the hollow cylinder and a raised ridge 24 is located adjacent the upper end of the connection portion. The use of this ridge 24 will be described later.

Each of the femoral components is of a different size, in this embodiment 110 mm, 150 mm and 190 mm and they are arranged to be connected to the mounting components 9 and 10 of FIG. 1. by pushing them over the spigot 13 and locating the key 22 in the key way 15 of the sleeve 14. It will be appreciated that the mounting component is now used inverted but is still suitable for connection to the lower part of the femur.

The engagement portion of the femoral component has an anatomical shaped patella flange, the sides are smooth and no sharp edges exist which might cause problems with soft tissue. As is mentioned above this component is made hollow to reduce weight.

The tibial component for use with the femoral component is provided in three sizes, as shown in FIG. 3, a standard size 0 mm, 90 mm, 120 mm 150 mm. This component is again made from Vitallium and has a Walldius type stem 30 and two flanges 31. It will be seen that the 0 mm size does not have a stem of this type. The component has a platform with two bearing surfaces and is used to replace the head of the tibia, the bearing surfaces representing the lateral and medial condyles on the tibia and the shaped engagement portion on the femoral component providing the lateral and medial condyles on the femur.

This knee resection system therefore provides three resection lengths of the femur and four resection lengths of the tibia along with stems of different diameter.

The femoral component is assembled in the theatre to the required length and the coupling of the femoral component and the tibial component uses the same procedure as with a spherocentric knee.

It will be appreciated that the invention can now provide a set of parts for an assembly which can be used to replace both of the joints associated with the femur of the patient and at the same time provides for the length of the components to be adjusted as required.

Due to the construction concerned it is possible to replace the joint components which carry the engagement portions without difficulty and this is advantageous if the patient is still growing.

Figure 4:
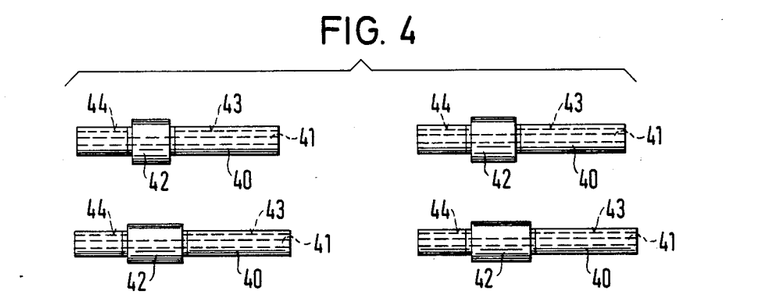
FIG. 4 is a diagrammatic representation of a set of mounting components which can be used with the parts shown in FIGS. 1 and 2.

FIG. 4 shows a set of alternative mounting components which can be used with the hip components shown in FIG. 1 and the femoral knee components shown in FIG. 2. The mounting components shown in FIG. 4 each comprise a coupling shaft 40 which is made from a plastics material with a metal reinforcement rod 41 at its centre. Each of the shafts is circular and has a raised portion 42 which is of greater diameter than the remainder. Keyways 43 and 44 are provided on each side of the raised portion 42.

The mounting components can be used with the parts shown in FIGS. 1, 2 and 3 to provide a total femur system which comprises hip components 5, coupling shafts shown in FIG. 4, femural components as shown in FIG. 2 and tibial components as shown in FIG. 3.

The diameter of the coupling shaft is such that it is a tight fit in the hip component and the key 8 enters the appropriate keyway 44, the part of the shaft carrying the keyway 44 therefore acting as a connection part. The portion of the shaft carrying the keyway 43 also acts as a connection portion for the femoral knee component which is a push fit onto it with the key 22 engaging the keyway 43. The two joint components are pushed towards each other until their ends contact the raised portion 42.

In the particular arrangement being described the following lengths can be made with the components referred to:

| Hip Component (Length in mm) | Knee Component (Length in mm) | Shaft (Length in mm) | Length Total Femur (Length in mm) |
|---|---|---|---|
| 190 | 110 | 40 | 340 |
| 190 | 110 | 50 | 350 |
| 190 | 110 | 60 | 360 |
| 190 | 110 | 70 | 370 |
| 190 | 150 | 40 | 380 |
| 190 | 150 | 50 | 390 |
| 190 | 150 | 60 | 400 |
| 190 | 150 | 70 | 410 |
| 190 | 190 | 40 | 420 |
| 190 | 190 | 50 | 430 |
| 190 | 190 | 60 | 440 |
| 190 | 190 | 70 | 450 |

With this construction therefore the femur is totally replaced but with the set of parts described the surgeon can make up a suitable length of prosthesis to replace it.

Figure 8:
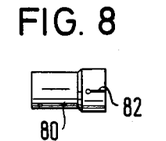
FIGS. 8 and 9 are diagrammatic front and end elevations of a retaining sleeve.
Figure 9:
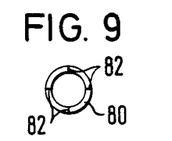

The last embodiment to be described is particularly suitable for growing patients and comprises an adjustable total femur system. In this case the same components as referred to in the example described above and with relation to FIG. 4 can be used with the addition of a set of split cylindrical spacers as shown in FIGS. 5 and 6, a washer 7 and a retaining sleeve as shown in FIGS. 8 and 9 and which is shown in more detail in FIG. 12.

Figure 5:
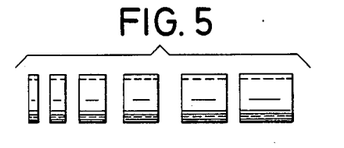
FIG. 5 is a diagrammatic representation of a set of spacers which can be used with one of the components shown in FIG. 4.
Figure 6:
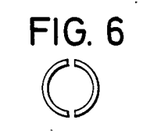
FIG. 6 is an end view of the spacers shown in FIG. 5.
Figure 7:
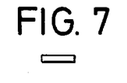
FIG. 7 is a diagrammatic representation of a washer for use with the spacers shown in FIGS. 5 and 6.

The spacers as shown in FIGS. 5 and 6 are shown in six sizes ranging from 10 mm to 60 mm with steps of 10 mm. They can be placed around the portion of the shaft which carries the key way 43 and kept in place by means of the retaining sleeve shown in FIGS. 8, 9 and 11 which slides over them. The plastics material washer 7 is placed at the end of the spacers and the femural knee component is now pushed into place. One end of the retaining sleeve 80 which is made from a plastics material is provided with an internal groove 81 and the end also carries four longitudinally extending slots 82. The sleeve can thus be snapped over the end of the femural knee component, the groove 81 being located on the ridge 24. This sleeve therefore holds the spacers in place and effectively alters the length between the joint components on the shaft.

As a number of shafts can be provided it will be appreciated that a vast variation can be achieved. With the arrangement being described the assembly can be used to achieve a maximum growth of 60 mm. The lengths which are achievable are equivalent to the ones shown in the Table but the following sizes can also be constructed, that is, 460, 470, 480, 490, 500 and 510 mm.

If a lengthening of the femur prosthesis is required due to growth, the following operation procedure can be employed:

The femur is placed in traction which must be enough to overcome muscle force and friction force in the push fit of the shaft and the femural knee component. After achieving the correct elongation an operation is performed. An incision half way on the femur is required to push up the retaining sleeve 80 and put in new spacers of the kind shown in FIG. 5. As the spacers are split it is possible to insert them from inside.

The retaining sleeve is again snap fitted around the femural component and the wound is closed. The effect is lengthen the total prosthesis.

Although the invention has been described with regard to an assembly for use with a femur it could of course be used with other bones, the appropriate joint components being of suitable shape as required by the joint or joints concerned. The system allows for a prosthesis to be made up of modular parts which can be used to provide part of the joint and/or parts of two or more joints provided the mounting component is suitable but the modular construction allows a single mounting component to employ joint components of different sizes and shapes, for example, as described in the arrangements set forth above. Again, the assembly can be used not only to replace a single joint but also replace a complete bone by providing the appropriate joint parts at each end.

In FIGS. 13 to 33 a modified modular reconstruction system is represented which will be described in more detail in the following.

Figure 13:
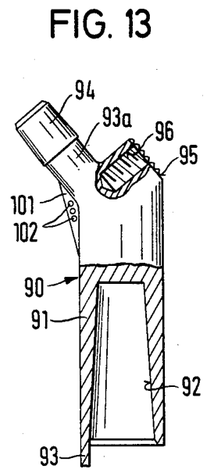
FIG. 13 is a part-sectional representation of another embodiment of a femural component of a hip joint endoprosthesis.
Figure 14:
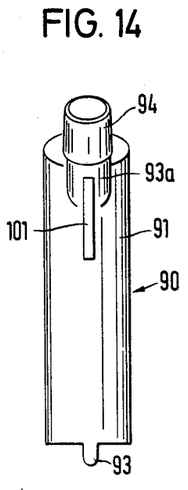
FIG. 14 is another end view of the joint component according to FIG. 13.
Figures 16, 17:
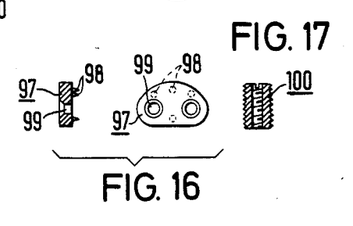
FIG. 16 is a sectional and top plan view of the small clamping plate for use together with the joint component according to FIGS. 13 and 14.
FIG. 17 is a representation of a threaded insert for the joint component according to FIGS. 13 and 14.

FIGS. 13 and 14 show the femural component 90 of a hip joint endoprosthesis. It comprises a downward opening hollow cylindrical portion 91 containing an inner cone 92. A nose 93 is provided at the lower edge. A neck portion 93a is provided at an obtuse angle as usual with a cone 94 arranged adjacent the end thereof for the accommodation of a suitable joint head with inner cone. In the region of the femural component 90 formed to resemble the trochanter a clamping surface 95 is arranged having two threaded blind bores 96 formed therein. The upper side of the clamping surface 95 is made madreporic. The semi-oval shape of the clamping surface 95 corresponds to the shape of a small clamping plate 97 of a suitable plastics material which is shown in FIG. 16. It is provided with several pointed projections 98 at its underside and with two openings 99, which are in conformity with the threaded bores 96. Threaded inserts 100 are inserted into the blind bores 96 according to FIG. 17 for the accommodation of screws which are pushed through the openings 99 of the small clamping plates 97, in order to effectively press the small clamping plates against the clamping surface 95. This construction serves to fasten sinews clamped in at the femural component 90.

A rib 101 formed between the neck portion 93a and the shaft portion 91 comprises three apertures 102 which likewise serve to tie sinews.

Figure 18:
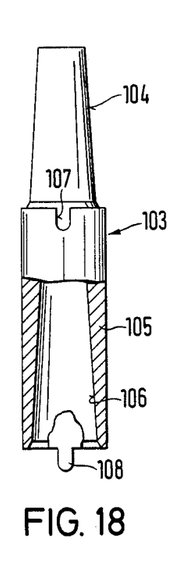
FIG. 18 is a part-sectional view of an elongation sleeve.

FIG. 18 shows a connection portion 103, which comprises a outer cone 104 and, in a cylindrical portion 105, an inner cone 106. The inner cone 106 corresponds in the dimensions thereof to the inner cone 92 of the component 90 according to FIGS. 13 and 14. The outer cone 104 may be fittingly inserted into the inner cone 92 of the component 90.

Figure 19:
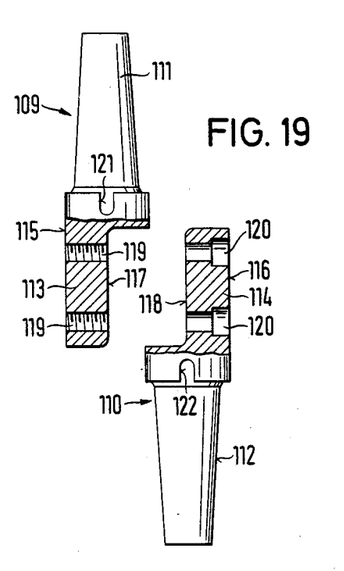
FIG. 19 is a part-sectional view of the two parts of a connection piece.

The cone angle of the inner cone 92 and the outer cone 104 are dimensioned such that the self-locking effect occurs. The plugging into each other of both portions takes place in such a manner that the nose-like porjection 93 fittingly engages within a recess 107 of the cylindrical portion 105 thereby providing a safety means against rotation. A nose-like projection corresponding to the nose-like projection 93 is formed integrally at the free end of the cylindrical portion 105 as shown at 108. FIG. 19 shows the halves 109 and 110 of a connection portion. They are each provided with a respective outer cone 111 and 112 and respective connection portions 113 and 114 which are each provided with a respective semi-cylindrical outer surface 115 and 116 and respective smooth inner surfaces 117 and 118. In the assembled condition the surfaces 117, 118 lie against each other, so that respective bores 119 and 120 are aligned with respect to each other. Screws, not shown, are threaded into the bores 19 and 120, the first-mentioned one forming a threaded bore. The outer cones 111 and 112 are therefore coaxial with respect to each other, likewise the respective recesses 121 and 122 in the connection portions 113 and 114. As may be readily seen, the outer cones 111 and 112, respectively, may be connected to an inner cone 92 and 108, respectively, of the parts according to the FIGS. 13, 14 and 18.

Figure 20:
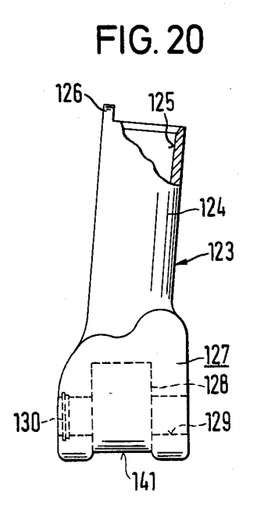
FIG. 20 is a part-sectional view of the side elevation of a joint component for the distal femur.
Figures 21, 22:
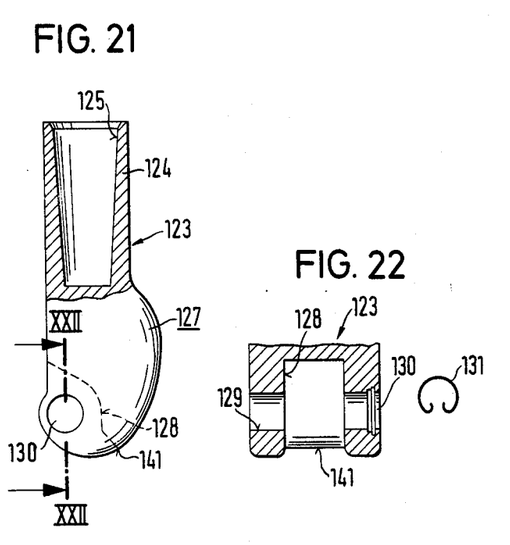
FIG. 21 is another part-sectional side elevation of the representation according to FIG. 20.
FIG. 22 is a sectional view taken on line 22—22 of FIG. 21.

In FIGS. 20 to 22 a distal femur component 123 is shown which comprises a cylindrical shaft portion 124 containing an inner cone 125. At the free end thereof a nose-like projection 126 is again provided (FIG. 20). Furthermore, the component 123 comprises a joint portion 127 which is formed to resemble the condyles of the distal femur. It comprises also a trough for the accommodation of the natural patella which is not shown in more detail in the drawings. In the joint portion 122 a joint recess 128 is formed integrally from below. The configuration of the bottom of the recess may be seen from the broken line in FIG. 21. It is selected to be such that even in the extreme flexure position no sharp edge or a wide interspace will form by which the natural platella might possibly be damaged. Throughbores 129 and 130, respectively, are formed integrally in the joint portion 127 transversely of the longitudinal axis and the extension of the joint recess 128. They serve to accommodate a joint pin (not shown) which may be axially secured with the aid of a circlip 131.

With the aid of the parts according to FIGS. 13 to 22 a complete femur may be reconstructed. By means of the different lengths of the joint components according to FIGS. 13 and 14 and 20 and 21, respectively, as well as the elongation pieces of FIG. 18 it is possible to achieve a very fine gradation of lengths.

So, three different dimensions of lengths may respectively be provided for the said parts with a difference in length of 10 mm, for example. If, with growing patients, an elongation of the femure prosthesis becomes necessary, a longer piece of elongation may be used for example, according to FIG. 18. Owing to the fact that the connection piece according to FIG. 19 makes possible a lateral separation, a surgeon need not excessively stretch the muscles and sinews when inserting the longer elongation piece.

Figure 23:
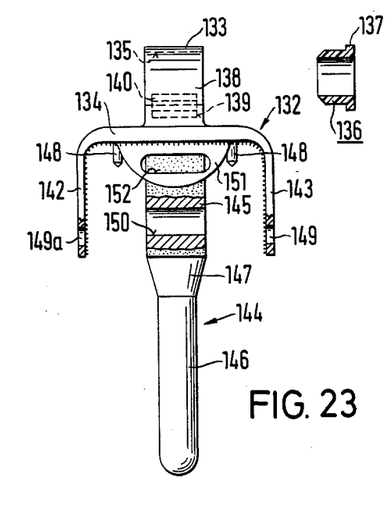
FIG. 23 is a part-sectional view of a tibial joint component.
Figure 24:
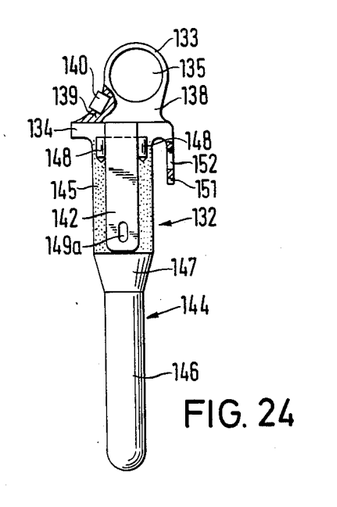
FIG. 24 is a side elevation of the representation according to FIG. 23.

FIGS. 23 and 24 show a tibial joint component 132. It has a joint ring 133 integrally formed at the plate 134 in an upright position. It is provided with a throughbore 135 into which a bushing of plastics material may be fittingly inserted from both sides with a radial flange 137 which comes to lie against the outer surface of the joint ring 133. The width of the joint ring 133 with the flanges 137 is such that it may be fittingly accommodated in the joint recess 128 of the distal femur part 123. A joint pin (not shown) is inserted through the openings 130 and 129 as well as through the throughbore of the bushings 137, so that an axis-connected knee joint construction is formed.

In the socket 138 which carries the joint ring 133 a rectangular recess 139 is formed in the front for the accommodation of a small plastics plate 140 projecting above the outer surface of the socket 138. The small plastics plate 140 serves as an abutment and buffer for the joint portion 127 of the distal femural component 123 in the stretched condition. The edge 141 (FIG. 21) of the recess 128 in this arrangement comes to lie against the small plastics plate 140.

From the plate 134 extend in spaced arrangement two tongues 142 and 143, respectively. The tongues 142, 143 are made madreporic on the sides thereof facing each other, as is the underside of the plate 134. Formed integrally with the plate is a shank 144 having a cylindrical portion 145 of a larger diameter and a cylindrical portion 146 of a smaller diameter. Between the portions 145 and 146 an approximately conical transition 147 is formed. The shank 144 is beaten into the distal tibia canal under compression with four spikes 148 provided on the under side of the plate 134 piercing into the tibia plateau in order to safely anchor the prosthesis component. The shank portion 145 is likewise made madreporic. The portions made madreporic take care of a good concrescence with the bone.

Openings 148, 149 are formed in the tongues 142, 143 in alignment with each other, said openings being aligned in addition with the transverse bore 150 in the shank portion 145. The openings are elongated holes and serve to accommodate a bone screw transversely threaded through the bone.

Formed integrally with the plate 134 is furthermore a downward pointing semi-oval tongue 151. It contains an elongated hole 152 for tying the fibula and sinews, respectively.

In case the entire or the distal femur is to be replaced, therefore, a construction according to FIGS. 13 to 24 may be used. If, however, the tibia or a proximate portion of the tibia is to be replaced, the construction according to FIGS. 25 to 33 will be used. This will be explained in more detail in the following.

Figure 28:
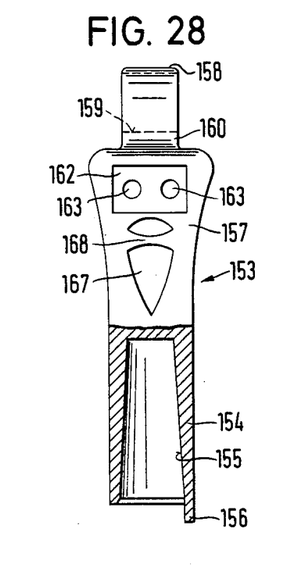
FIG. 28 is a part-sectional side elevation of the tibial part of a joint endoprosthesis.
Figures 29, 30:
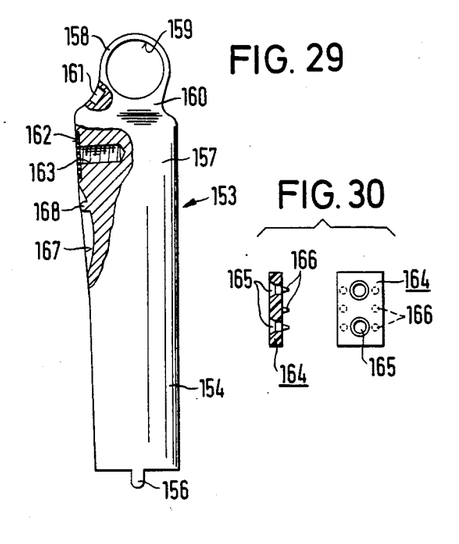
FIG. 29 shows another part-sectional side elevation of the representation according to FIG. 28.
FIG. 30 shows a sectional and top plan view of a small clamping plate for the joint component according to FIGS. 28 and 29.

FIGS. 28 and 29 show a tibial knee joint component which is in addition intended to replace the proximate tibia portion. It is generally referenced 153. It comprises a downward opening cylindrical shank portion 154 having an inner cone 155. A nose-like projection 156 is furthermore formed at the lower edge. The upper portion 157 is made to approach the anatomic proximate tibia. A joint ring 158 is formed at the upper surface thereof, similar to the joint ring 133 according to FIGS. 23 and 24. The joint ring is provided with a joint bore 159. The box portion 160 above which the joint ring 158 is formed integrally with the prosthesis portion 157 has a rectangular recess (FIG. 29) formed in front thereof for the accommodation of a raised small plastics plate (not shown) similar to the small plastics plate 140 according to FIG. 24.

The portion 157 is provided with a clamping surface 162 in front which is likewise made madreporic and comprises two threaded blind bores 163. Threaded inserts according to FIG. 17 may be inserted into the threaded bores 163 for the accommodation of screws by means of which a small plastics plate 164 according to FIG. 30 may be pressed against the clamping surface 162. The small plastics plate 164 provided with two openings 165 adapted to be aligned with the threaded bores 163 has in addition several projections 166. They serve for better fastening the sinews with the aid of the small plastics plate 164 at the clamping surface 162.

Beneath the clamping surface 162 a trough 167 is formed integrally therein which is bridged over by a slightly vaulted web 168. The web 168 serves to tie the fibula.

Figures 25, 26, 27:
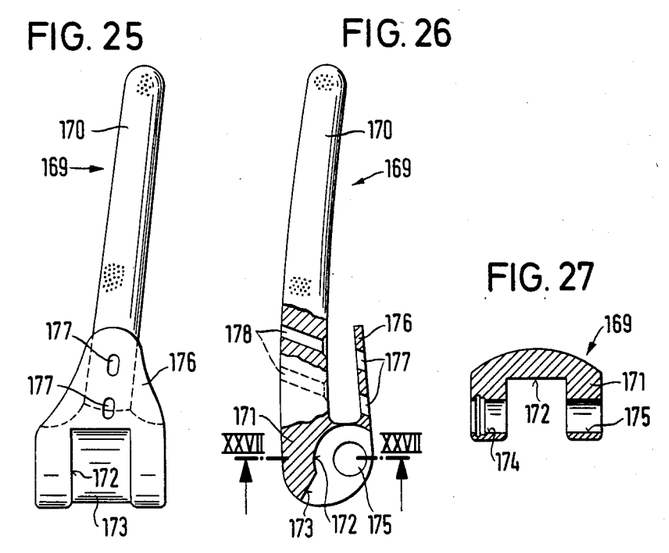
FIG. 25 is a representation of the femural joint component of a knee joint endoprosthesis.
FIG. 26 is a part-sectional view of a side elevation of the joint component according to FIG. 25.
FIG. 27 is a sectional view taken on line 27—27 of the representation according to FIG. 26.

The tibial component shown in FIGS. 28 and 29 is adapted to cooperate with a femoral component of a knee endoprosthesis as shown in FIGS. 26 and 26 and referenced 169. It has a shank 170 the outer surface of which is made madreporic. The portion 171 adjacent the joint is provided with a joint recess 172 in a manner similar to the component 123 according to FIGS. 20 to 22, the bottom of said recess being clearly visible by the definition 173 in FIG. 26. Two through-bores 174 and 175, respectively, are extending transversely through the joint portion 121.

The joint connection of the components 153 and 169 resembles the one as described in connection with the components 123 and 132 according to FIGS. 20 to 24. It will therefore no longer be enlarged thereon in more detail.

The joint portion 171 which is again designed to resemble the anatomic condyles of the distal femur furthermore has a tongue 176 integrally formed thereat which extends in an upward direction and comes to lie dorsally against the femur when the shank 170 is driven into the canal of the distal femur. Openings 177 formed in the tongues 176 are aligned with the obliquely extending openings 178 in the shaft 170 for the accommodation of a bone screw for the purpose of additionally securing the joint component 169 in the femur.

The system shown in FIGS. 25 to 29 serves to replace a resected proximate tibia. Therefore, the components 153 are provided in the form of a set of staggered lengths. The fastening of the joint component 153 with the remaining tibia is performed with the aid of the connection portion according to FIGS. 31 to 33.

Figure 31:
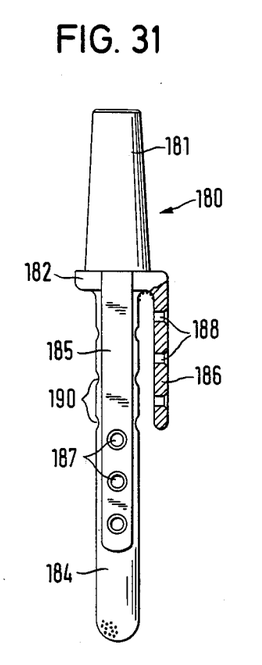
FIG. 31 is a part-sectional view of a tibial connection piece.
Figure 32:
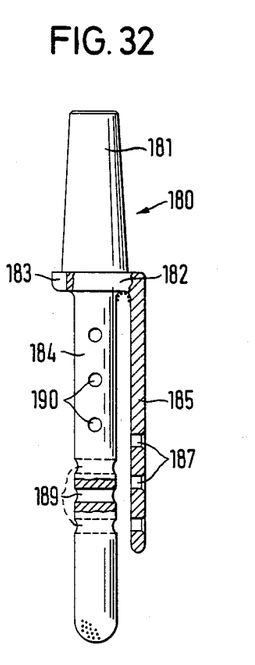
FIG. 32 is another side elevation of the representation according to FIG. 31.
Figure 33:
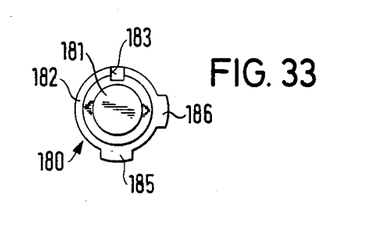
FIG. 33 is a top plan view of the connection portion according to FIGS. 31 and 32.

The connection portion is generally referenced 180 in FIGS. 31 to 33. It has a conical portion 181 the dimensions and cone angles of which correspond to the inner cone 155 of the joint component 153 according to FIGS. 28 and 29. A recess 183 is formed in a flange 182 at the lower end of the cone portion 181 which is adapted to accommodate the nose-like projection 156 of the joint component 153 when the parts are plugged together. Below the flange 182 a shaft 184 is formed the upper surface of which is made madreporic and which is driven into the remaining tibia canal. Formed integrally with the flange are two tongues 185 and 186 respectively offset circumferentially through 90° which come to lie in close contact against the bone from outside. Openings 187 and 188, respectively, formed in the tongues 185, 186 are in alignment with openings 189 and 190, respectively, formed in the shaft 184 for the accommodation of bone screws so that the connection portion may be fastened at the bone more effectively. It goes without saying that an elongation member of differing length according to FIG. 18 may also be inserted between a joint component according to FIGS. 28 and 29 to replace the proximate tibia, with the elongation member according to FIG. 18 cooperating with the connection portion 180 according to FIGS. 31 to 33 and being fastened at the tibia via the latter. The longitudinal dimension of the connection portion 180 need not be altered. Different diameters may have to be provided for the shaft 184 if occasion arises, dependent on the dimensions of the tibia which it is the intention to reconstruct with the aid of the system as shown.

Figure 15:
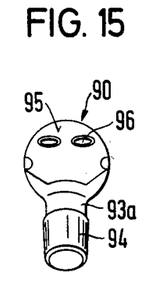
FIG. 15 is a top plan view on the representation according to FIGS. 13 and 14.

It goes without saying that also the femoral joint component of the hip joint endoprosthesis referenced 90 in FIGS. 13 to 15 may be connected to the remaining femur with the aid of a connection portion as shown in FIGS. 31 to 33.

It is furthermore still to be mentioned that all the portions of the modular system shown which serve as bone replacement members are of the same outer diameter.

What is claimed is:

1. A bone prosthesis assembly for replacement of at least part of a natural joint of a patient comprising a connection member adapted to be connected to the bone of the patient at one end of said connection member, a joint component including a cylindrical shank portion adapted to be connected by a mutually engaging frictional self-locking cone-type connection to said connection member at the other end of said connection member, and a set of elongation pieces of varying length each adapted to be arranged between said joint component and the connection member, with said connection member being provided with an outer male conical portion and said joint component being provided with an inner female conical portion adapted for reception of and mutual engagement with said outer male conical portion, with each of said elongation pieces comprising a cylindrical body portion provided with an inner female conical portion opening to one end of the body portion, and an outer male conical portion extending from the other end of the body portion, with the outer diameter of each of said elongation piece body portions being equal to the outer diameter of said joint component shank portion, and with the shank portion abutting the adjacent body portion when the joint component and elongation piece are connected.

2. A bone prosthesis assembly according to claim 1, wherein said joint component is the femoral joint part of a hip joint prosthesis.

3. A bone prosthesis assembly according to claim 1, wherein said joint component comprises a conical neck portion adapted to receive a joint head with an inner female conical portion in frictional engagement.

4. A bone prosthesis assembly according to claim 1, wherein said joint component is the femoral joint part of a knee joint prosthesis.

5. A bone prosthesis according to claim 1, wherein said joint component is the tibial joint part of a knee joint prosthesis.

* * * * *